(12) United States Patent
Park et al.

(10) Patent No.: US 6,235,751 B1
(45) Date of Patent: May 22, 2001

(54) QUINOLIZINE CARBOXYLIC ACID DERIVATIVES

(75) Inventors: Tae-Ho Park, Daejeon; Young-Hwan Ha, Kwangju; Do-Yeob Kim, Daejeon, all of (KR)

(73) Assignee: Korean Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/500,283

(22) Filed: Feb. 8, 2000

Related U.S. Application Data

(63) Continuation of application No. PCT/KR98/00247, filed on Aug. 8, 1998.

(30) Foreign Application Priority Data

Aug. 9, 1997 (KR) .................................................. 97-38037

(51) Int. Cl.$^7$ ...................... C07D 455/02; C07D 471/02; A61K 31/44
(52) U.S. Cl. ............................................. 514/306; 546/138
(58) Field of Search ............................. 514/306; 546/138

(56) References Cited

U.S. PATENT DOCUMENTS 5,789,591 * 8/1998 Chu et al. ............................ 546/138
5,977,133 * 11/1999 Fung et al. ........................... 514/306

OTHER PUBLICATIONS

Qun Li et al.,Journal of Medicinal Chemistry, vol. 39, No. 16, pp. 3070–3088 !Aug. 2, 1996).*

* cited by examiner

Primary Examiner—Alan L. Rotman
(74) Attorney, Agent, or Firm—Rosenman & Colin

(57) ABSTRACT

A quinolizine carboxylic acid derivative of formula (I) or a pharmaceutically acceptable salt thereof:

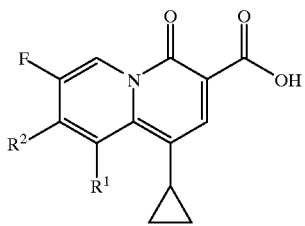

(I)

wherein $R^1$ and $R^2$ have the same meanings the as defined in the specification.

5 Claims, No Drawings

QUINOLIZINE CARBOXYLIC ACID DERIVATIVES

CROSS REFERENCE TO RELATED APPLICATION

This application is a continuation of international application No. PCT KR/98/00247, filed Aug. 8, 1998.

FIELD OF THE INVENTION

The present invention relates to 4-oxo-quinolizine carboxylic acid derivatives and pharmaceutically acceptable salts thereof having an excellent antibacterial activity, a process for preparing same, and an antibacterial composition containing same as an active ingredient.

BACKGROUND OF THE INVENTION

Quinolizine derivatives are known to exhibit excellent antibacterial activities(see PCT publication No. WO 95/10519) However, some of the conventional quinolizine compounds have limited activities against Gram-positive bacteria, while other quinolizine derivatives exhibit the problem of poor water-solubility or side effects such as high cytotoxicity.

The present inventors have, therefore, endeavored to develop non-toxic compounds having a higher potency against a wide spectrum of bacteria; and have unexpectedly found that certain quinolizine carboxylic acid derivatives having an amine moiety at the 8-position of the 4-oxo-quinolizine nucleus exhibit a broad spectrum antibacterial activity and reduced cytotoxicity.

SUMMARY OF THE INVENTION

It is, therefore, a primary object of the present invention to provide novel 4-oxo-quinolizine carboxylic acid derivatives, and pharmaceutically acceptable salts thereof, having a potent antibacterial activity, especially against Gram-positive bacteria, with a low cytotoxicity.

It is another object of the present invention to provide an antibacterial composition containing the inventive compounds as an active ingredient.

It is a further object of the present invention to provide a process for the preparation of the inventive novel compounds.

In accordance with the present invention, there is provided a 4-oxo-quinolizine carboxylic acid derivative of formula (I) or a pharmaceutically acceptable salt thereof:

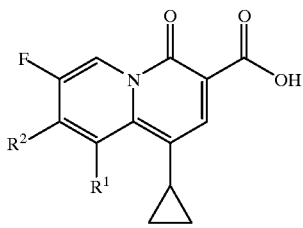

(I)

wherein $R^1$ is a $C_{1-4}$ alkyl group optionally substituted with one ore more halogens, or a $C_{1-4}$ alkoxy group;

$R^2$ is

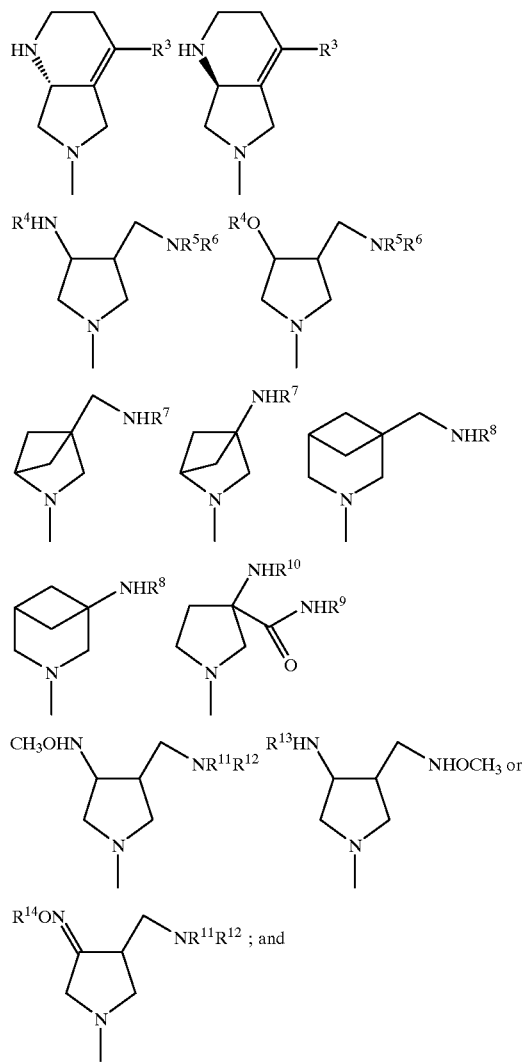

$R^3$, $R^4$, $R^5$, $R^6$, $R^7$, $R^8$, $R^9$, $R^{10}$, $R^{11}$, $R^{12}$, $R^{13}$ and $R^{14}$ are each independently H or a $C_{1-4}$ alkyl group optionally substituted with a pyridyl, arylalkyl or aryl group.

DETAILED DESCRIPTION OF THE INVENTION

Among the compounds of the present invention, preferred are those wherein: $R^1$ is $CH_3$ or $OCH_3$; $R^2$ is

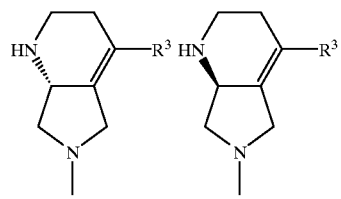

-continued

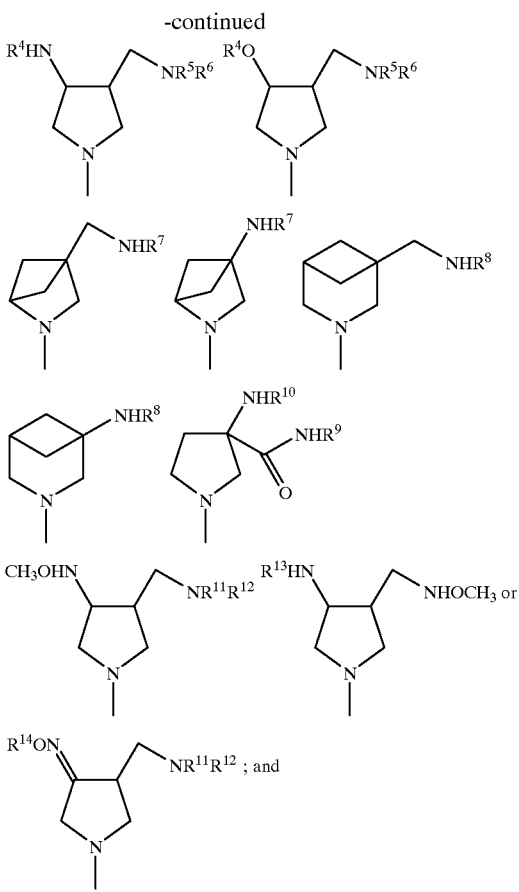

R³, R⁵, R⁶, R⁸, R¹¹ and R¹² are each independently H or CH₃; R⁴ is H or a methyl group optionally substituted with a pyridyl or benzyl group; R⁷, R⁹, R¹⁰ and R¹³ are H or CH₃; R¹⁴ is CH₃.

Particularly preferred compounds of formula (I) of the present invention are:
8-{[(R)-2,8-diazabicyclo[4.3.0]non-5-en]-8-yl}-1-cyclopropyl-7-fluoro-9-methyl-4-oxo-4H-quinolizine-3-carboxylic acid;
8-{[(S)-2,8-diazabicyclo[4.3.0]non-5-en]-8-yl}-1-cyclopropyl-7-fluoro-9-methyl-4-oxo-4H-quinolizine-3-carboxylic acid;
8-{[(R)-5-methyl-2,8-diazabicyclo[4.3.0]non-5-en]-8-yl}-1-cyclopropyl-7-fluoro-9-methyl-4-oxo-4H-quinolizine-3-carboxylic acid;
8-[(1-aminomethyl-3-azabicyclo[2.1.1]hex)-3-yl]-1-cyclopropyl-7-fluoro-9-methyl-4-oxo-4H-quinolizine-3-carboxylic acid;
8-[(1-amino-3-azabicyclo[2.1.1]hex)-3-yl]-1-cyclopropyl-7-fluoro-9-methyl-4-oxo-4H-quinolizine-3-carboxylic acid;
8-[(1-amino-3-azabicyclo[3.1.1]hept)-3-yl]-1-cyclopropyl-7-fluoro-9-methyl-4-oxo-4H-quinolizine-3-carboxylic acid;
8-[(1-aminomethyl-3-azabicyclo[3.1.1]hept)-3-yl]-1-cyclopropyl-7-fluoro-9-methyl-4-oxo-4H-quinolizine-3-carboxylic acid;
8-[(1-N-methylaminomethyl-3-azabicyclo[3.1.1]hept)-3-yl]-1-cyclopropyl-7-fluoro-9-methyl-4-oxo-4H-quinolizine-3-carboxylic acid;
8-[(1-N-methylamino-3-azabicyclo[3.1.1]hept)-3-yl]-1-cyclopropyl-7-fluoro-9-methyl-4-oxo-4H-quinolizine-3-carboxylic acid;
8-[(3-amino-3-carbamoylpyrrolidine)-1-yl]-1-cyclopropyl-7-fluoro-9-methyl-4-oxo-4H-quinolizine-3-carboxylic acid;
8-[(3-N-methylaminomethyl-4-N-methylaminopyrrolidine)-1-yl]-1-cyclopropyl-7-fluoro-9-methyl-4-oxo-4H-quinolizine-3-carboxylic acid;
8-[(3-amino-4-aminomethylpyrrolidine)-1-yl]-1-cyclopropyl-7-fluoro-9-methyl-4-oxo-4H-quinolizine-3-carboxylic acid;
8-[(3-aminomethyl-4-N-methoxyaminopyrrolidine)-1-yl]-1-cyclopropyl-7-fluoro-9-methyl-4-oxo-4H-quinolizine-3-carboxylic acid;
8-[(3-amino-4-N-methoxyaminopyrrolidine)-1-yl]-1-cyclopropyl-7-fluoro-9-methyl-4-oxo-4H-quinolizine-3-carboxylic acid;
8-[(3-N-methoxyamino-4-N-methylaminomethylpyrrolidine]-1-yl}-1-cyclopropyl-7-fluoro-9-methyl-4-oxo-4H-quinolizine-3-carboxylic acid;
8-{[3-(3-pyridylmethyl)oxy-4-aminomethylpyrrolidine]-1-yl}-1-cyclopropyl-7-fluoro-9-methyl-4-oxo-4H-quinolizine-3-carboxylic acid;
8-{[3-(2-pyridylmethyl)oxy-4-aminomethylpyrrolidine]-1-yl}-1-cyclopropyl-7-fluoro-9-methyl-4-oxo-4H-quinolizine-3-carboxylic acid;
8-{[3-(4-pyridylmethyl)oxy-4-aminomethylpyrrolidine]-1-yl}-1-cyclopropyl-7-fluoro-9-methyl-4-oxo-4H-quinolizine-3-carboxylic acid;
8-{[3-N-(3-pyridylmethyl)amino-4-aminomethylpyrrolidine]-1-yl}-1-cyclopropyl-7-fluoro-9-methyl-4-oxo-4H-quinolizine-3-carboxylic acid;
8-[(3-N-benzylamino-4-aminomethylpyrrolidine)-1-yl]-1-cyclopropyl-7-fluoro-9-methyl-4-oxo-4H-quinolizine-3-carboxylic acid;
8-{[(R)-2,8-diazabicyclo[4.3.0]non-5-en]-8-yl}-1-cyclopropyl-7-fluoro-9-methoxy-4-oxo-4H-quinolizine-3-carboxylic acid;
8-{[(S)-2,8-diazabicyclo[4.3.0]non-5-en]-8-yl}-1-cyclopropyl-7-fluoro-9-methoxy-4-oxo-4H-quinolizine-3-carboxylic acid;
8-[(3-N-methoxyimino-4-aminomethylpyrrolidine)-1-yl]-1-cyclopropyl-7-fluoro-9-methyl-4-oxo-4H-quinolizine-3-carboxylic acid; and pharmaceutically acceptable salts thereof.

The present invention further includes, within its scope, pharmaceutically acceptable salts of the compounds of formula (I). The non-toxic salts which fall within the scope of the present invention may include inorganic acid salts such as hydrochloride, sulfate, phosphate and nitrate, and organic acid salts such as tartrate, fumarate, citrate, mesylate and acetate.

The pharmaceutically acceptable salt of the present invention may be prepared in accordance with a known method, e.g., by reacting the compounds of formula (I) with a suitable acid in the presence of a solvent, e.g., methanol, ethanol, dichloromethane, ethyl acetate or diethyl ether.

The compound of formula (I) may be prepared by a process which comprises reacting a 4-oxoquinolizine-3-carboxylic acid derivative of formula (II) with an amine of formula (III) in a suitable solvent in the presence of a base.

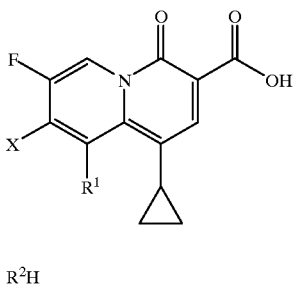

wherein, $R^1$ and $R^2$ have the same meanings as defined above; and X is halogen such as F and Cl, or sulfonyl group.

The condensation reaction of compounds (II) and (III) may be conducted at a temperature ranging from 20 to 120° C.

Exemplary solvents which may be suitably used in the process of the present invention include acetonitrile, dimethylformamide, dimethylsulfoxide and pyridine.

The base which can be used in practicing the present invention may be an inorganic base, or an organic base such as triethylamine, pyridine, diazabicyclo[5.4.0]undec-7-ene and diisopropylamine.

The compound of formula (II) may be prepared in accordance with the method disclosed in PCT Publication No. WO 95/10519.

The compound of formula (III) may be prepared in accordance with the procedure disclosed in U.S. Pat. No. 5,631,266 and 35th ICAAC, San Francisco, 1995, Abstract No. F204.

The compounds of the present invention may be administered, either orally or intraperitoneally, in an effective amount ranging from 0.01 mg/kg to 100 mg/kg, preferably from 0.01 mg/kg to 50 mg/kg to a subject patient per day.

The present invention also includes within its scope an antibacterial composition comprising one or more of the inventive compounds as an active ingredient, in association with a pharmaceutically acceptable carrier, excipient and/or other additives, if necessary. The active ingredient present in the composition may range from 5% to 20% by weight thereof.

The following Examples are given for the purpose of illustration only, and are not intended to limit the scope of the invention.

EXAMPLE 1

8-{[(R)-2,8-diazabicyclo[4.3.0]non-5-en]-8-yl}-1-cyclopropyl-7-fluoro-9-methyl-4-oxo-4H-quinolizine-3-carboxylic acid 100 mg of 8-chloro-1-cyclopropyl-7-fluoro-9-methyl-4-oxo-4H-quinolizine-3-carboxylic acid, 70 mg of (R)-2,8-diazabicyclo[4.3.0]non-5-ene.2HCl and 200 mg of diazabicyclo[5.4.0]undec-7-ene were added to 5 ml of acetonitrile and the mixture was refluxed for 10 hours. Then, the resulting mixture was cooled and the solvent was distilled off under a reduced pressure. The residue was dissolved in 10 ml of methylene chloride, washed with water, dried over anhydrous magnesium sulfate and passed through a column filled with alumina. After removing the solvent, the residue was dissolved in methanol and activated charcoal was added thereto. The mixture was stirred to remove brown impurities and the solvent was distilled off to obtain 98 mg of the title compound as a yellow solid.

Element Analysis($C_{21}H_{22}N_3O_3F$) Exp. (%): C, 65.71; H, 5.73; N, 10.88 Calc. (%): C, 65.78; H, 5.78; N, 10.96

EXAMPLE 2

8-{[(S)-2,8-diazabicyclo[4.3.0]non-5-en]-8-yl}-1-cyclopropyl-7-fluoro-9-methyl-4-oxo-4H-quinolizine-3-carboxylic acid The procedure of Example 1 was repeated except that (S)-2,8-diazabicyclo[4.3.0]non-5-ene.2HCl was used as a starting material in place of (R)-2,8-diazabicyclo[4.3.0]-non-5-ene.2HCl to obtain 84 mg of the title compound as a yellow solid.

Element Analysis($C_{21}H_{22}N_3O_3F$) Exp. (%): C, 65.71; H, 5.73; N, 10.88 Calc. (%): C, 65.78; H, 5.78; N, 10.96

EXAMPLE 3

8-{[(R)-5-methyl-2,8-diazabicyclo[4.3.0]non-5-en]-8-yl}-1-cyclopropyl-7-fluoro-9-methyl-4-oxo-4H-quinolizine-3-carboxylic acid The procedure of Example 1 was repeated except that 84 mg of (R)-5-methyl-2,8-diazabicyclo[4.3.0]non-5-ene.2HCl was used as a starting material in place of (R)-2,8-diazabicyclo[4.3.0]non-5-ene.2HCl to obtain 88 mg of the title compound as a yellow solid.

Element Analysis($C_{22}H_{24}N_3O_3F$) Exp. (%): C, 66.21; H, 6.13; N, 10.58 Calc. (%): C, 66.48; H, 6.09; N, 10.57

EXAMPLE 4

8-[(1-aminomethyl-3-azabicyclo[2.1.1]hex)-3-yl]-1-cyclopropyl-7-fluoro-9-methyl-4-oxo-4H-quinolizine-3-carboxylic acid The procedure of Example 1 was repeated except that 74 mg of 1-aminomethyl-3-azabicyclo[2.1.1]hexane.2HCl was used as a starting material in place of (R)-2,8-diazabicyclo[4.3.0]non-5-ene.2HCl to obtain 70 mg of the title compound as a yellow solid.

Element Analysis($C_{20}H_{22}N_3O_3F$) Exp. (%): C, 64.51; H, 5.99; N, 11.34 Calc. (%): C, 64.68; H, 5.97; N, 11.31

EXAMPLE 5

8-[(1-amino-3-azabicyclo[2.1.1]hex)-3-yl]-1-cyclopropyl-7-fluoro-9-methyl-4-oxo-4H-quinolizine-3-carboxylic acid The procedure of Example 1 was repeated except that 1-amino-3-azabicyclo[2.1.1]hexane.2HCl was used as a starting material in place of (R)-2,8-diazabicyclo-[4.3.0]non-5-ene.2HCl to obtain 72 mg of the title compound as a yellow solid.

Element Analysis($C_{19}H_{20}N_3O_3F$) Exp. (%): C, 63.87; H, 5.86; N, 11.69 Calc. (%): C, 63.86; H, 5.94; N, 11.76

EXAMPLE 6

8-[(1-amino-3-azabicyclo[3.1.1]hept)-3-yl]-1-cyclopropyl-7-fluoro-9-methyl-4-oxo-4H-quinolizine-3-carboxylic acid The procedure of Example 1 was repeated except that 82 mg of 1-amino-3-azabicyclo[3.1.1]heptane.2HCl was used as a starting material in place of (R)-2,8-diazabicyclo-[4.3.0]non-5-ene.2HCl to obtain 112 mg of the title compound as a yellow solid.

Element Analysis($C_{20}H_{22}N_3O_3F$) Exp. (%): C, 64.86; H, 5.91; N, 11.32 Calc. (%): C, 64.68; H, 5.97; N, 11.31

EXAMPLE 7

8-[(1-aminomethyl-3-azabicyclo[3.1.1]hept)-3-yl]-1-cyclopropyl-7-fluoro-9-methyl-4-oxo-4H-quinolizine-3-carboxylic acid The procedure of Example 1 was repeated except that 90 mg of 1-aminomethyl-3-azabicyclo[3.1.1]heptane.2HCl was used as a starting material in place of (R)-2,8-diazabicyclo-[4.3.0]

non-5-ene.2HCl to obtain 112 mg of the title compound as a yellow solid.
Element Analysis($C_{21}H_{24}N_3O_3F$) Exp. (%): C, 66.47; H, 6.26; N, 10.90 Calc. (%): C, 66.44; H, 6.28; N, 10.90

EXAMPLE 8
8-[(1-N-methylaminomethyl-3-azabicyclo[3.1.1]-hept)-3-yl]-1-cyclopropyl-7-fluoro-9-methyl-4-oxo-4H-quinolizine-3-carboxylic acid The procedure of Example 1 was repeated except that 99 mg of 1-N-methylaminomethyl-3-azabicyclo[3.1.1]-heptane.2HCl was used as a starting material in place of (R)-2,8-diazabicyclo[4.3.0]non-5-ene.2HCl to obtain 137 mg of the title compound as a yellow solid.
Element Analysis($C_{22}H_{26}N_3O_3F$) Exp. (%): C, 66.21; H, 6.57; N, 10.61 Calc. (%): C, 66.15; H, 6.56; N, 10.52

EXAMPLE 9
8-[(1-N-methylamino-3-azabicyclo[3.1.1]hept)-3-yl]-1-cyclopropyl-7-fluoro-9-methyl-4-oxo-4H-quinolizine-3-carboxylic acid The procedure of Example 1 was repeated except that 92 mg of 1-N-methylamino-3-azabicyclo[3.1.1]heptane.2HCl was used as a starting material in place of (R)-2,8-diazabicyclo[4.3.0]non-5-ene.2HCl to obtain 112 mg of the title compound as a yellow solid.
Element Analysis($C_{21}H_{24}N_3O_3F$) Exp. (%): C, 66.38; H, 6.09; N, 10.61 Calc. (%): C, 65.45; H, 6.23; N, 10.90

EXAMPLE 10
8-[(3-amino-3-carbamoylpyrrolidine)-1-yl)-1-cyclopropyl-7-fluoro-9-methyl-4-oxo-4H-quinolizine-3-carboxylic acid The procedure of Example 1 was repeated except that 92 mg of 3-amino-3-carbamoylpyrrolidine.2HCl was used as a starting material in place of (R)-2,8-diazabicyclo[4.3.0]-non-5-ene.2HCl to obtain 107 mg of the title compound as a yellow solid.
Element Analysis($C_{19}H_{21}N_4O_4F$) Exp. (%): C, 58.71; H, 5.41; N, 14.39 Calc. (%): C, 58.76; H, 5.45; N, 14.43

EXAMPLE 11
8-[(3-N-methylaminomethyl-4-N-methylaminopyrrolidine)-1-yl]-1-cyclopropyl-7-fluoro-9-methyl-4-oxo-4H-quinolizine-3-carboxylic acid The procedure of Example 1 was repeated except that 102 mg of 3-N-methylaminomethyl-4-N-methylaminopyrrolidine.2HCl was used as a starting material in place of (R)-2,8-diazabicyclo-[4.3.0]non-5-ene.2HCl to obtain 127 mg of the title compound as a yellow solid.
Element Analysis($C_{20}H_{25}N_4O_3F$) Exp. (%): C, 62.91; H, 6.98; N, 14.20 .Calc. (%): C, 62.69; H, 6.72; N, 13.93

EXAMPLE 12
8-[(3-amino-4-aminomethylpyrrolidine)-1-yl]-1-cyclopropyl-7-fluoro-9-methyl-4-oxo-4H-quinolizine-3-carboxylic acid The procedure of Example 1 was repeated except that 96 mg of 3-amino-4-aminomethylpyrrolidine.2HCl was used as a starting material in place of (R)-2,8-diazabicyclo-[4.3.0]non-5-ene.2HCl to obtain 116 mg of the title compound as a yellow solid.
Element Analysis($C_{19}H_{23}N_4O_3F$) Exp. (%): C, 60.91; H, 6.21; N, 14.88 Calc. (%): C, 60.95; H, 6.19; N, 14.96

EXAMPLE 13
8-(3-aminomethyl-4-N-methoxyaminopyrrolidine)-1-yl]-1-cyclopropyl-7-fluoro-9-methyl-4-oxo-4H-quinolizine-3-carboxylic acid The procedure of Example 1 was repeated except that 110 mg of 3-aminomethyl-4-N-methoxyaminopyrrolidine. 2HCl was used as a starting material in place of (R)-2,8-diazabicyclo[4.3.0]non-5-ene.2HCl to obtain 107 mg of the title compound as a yellow solid.
Element Analysis($C_{20}H_{25}N_4O_4F$) Exp. (%): C, 59.31; H, 6.26; N, 13.78 Calc. (%): C, 59.40; H, 6.23; N, 13.85

EXAMPLE 14
8-[(3-amino-4-N-methoxyaminopyrrolidine)-1-yl]-1-cyclopropyl-7-fluoro-9-methyl-4-oxo-4H-quinolizine-3-carboxylic acid The procedure of Example 1 was repeated except that 110 mg of 3-amino-4-N-methoxyaminopyrrolidine.2HCl was used as a starting material in place of (R)-2,8-diazabicyclo-[4.3.0]non-5-ene.2HCl to obtain 122 mg of the title compound as a yellow solid.
Element Analysis($C_{20}H_{25}N_4O_4F$) Exp. (%): C, 59.41; H, 6.29; N, 13.91 Calc. (%): C, 59.40; H, 6.23; N, 13.85

EXAMPLE 15
8-[(3-N-methoxyamino-4-N-methylaminomethylpyrrolidine)-1-yl]-1-cyclopropyl-7-fluoro-9-methyl-4-oxo-4H-quinolizine-3-carboxylic acid The procedure of Example 1 was repeated except that 92 mg of 3-N-methoxyamino-4-N-methylaminopyrrolidine.2HCl was used as a starting material in place of (R)-2,8-diazabicyclo[4.3.0]non-5-ene.2HCl to obtain 107 mg of the title compound as a yellow solid.
Element Analysis($C_{21}H_{27}N_4O_4F$) Exp. (%): C, 60.21; H, 6.54; N, 13.37 Calc. (%): C, 60.27; H, 6.50; N, 13.39

EXAMPLE 16
8-{[3-(3-pyridylmethyl)oxy-4-aminomethylpyrrolidine]-1-yl}-1-cyclopropyl-7-fluoro-9-methyl-4-oxo-4H-quinolizine-3-carboxylic acid The procedure of Example 1 was repeated except that 120 mg of 3-(3-pyridylmethyl)oxy-4-aminomethyl pyrrolidine.2HCl was used as a starting material in place of (R)-2,8-diazabicyclo-[4.3.0]non-5-ene.2HCl to obtain 137 mg of the title compound as a yellow solid.
Element Analysis($C_{25}H_{27}N_4O_4F$) Exp. (%): C, 55.59; H, 5.21; N, 18.11 Calc. (%): C, 64.38; H, 5.79; N, 12.02

EXAMPLE 17
8-{[3-(2-pyridylmethyl)oxy-4-aminomethylpyrrolidine]-1-yl}-1-cyclopropyl-7-fluoro-9-methyl-4-oxo-4H-quinolizine-3-carboxylic acid The procedure of Example 1 was repeated except that 120 mg of 3-(2-pyridylmethyl)oxy-4-aminomethyl pyrrolidine.2HCl was used as a starting material in place of (R)-2,8-diazabicyclo-[4.3.0]non-5-ene.2HCl to obtain 146 mg of the title compound as a yellow solid.
Element Analysis($C_{25}H_{27}N_4O_4F$) Exp. (%): C, 64.48; H, 5.85; N, 12.14 Calc. (%): C, 64.38; H, 5.79; N, 12.02

EXAMPLE 18
8-{[3-(4-pyridylmethyl)oxy-4-aminomethylpyrrolidine]-1-yl}-1-cyclopropyl-7-fluoro-9-methyl-4-oxo-4H-quinolizine-3-carboxylic acid The procedure of Example 1 was repeated except that 120 mg of 3-(4-pyridylmethyl)oxy-4-aminomethylpyrrolidine.2HCl was used as a starting material in place of (R)-2,8-diazabicyclo-[4.3.0]non-5-ene.2HCl to obtain 131 mg of the title compound as a yellow solid.
Element Analysis($C_{25}H_{27}N_4O_4F$) Exp. (%): C, 64.21; H, 5.63; N, 11.86 Calc. (%): C, 64.38; H, 5.79; N, 12.02

EXAMPLE 19
8-{[3-N-(3-pyridylmethyl)amino-4-aminomethylpyrrolidine]-1-yl}-1-cyclopropyl-7-fluoro-9-methyl-4-oxo-4H-quinolizine-3-carboxylic acid The procedure of Example 1 was repeated except that 112 mg of 3-N-(3-pyridylmethyl)amino-4-aminomethylpyrrolidine.2HCl was used as a starting material in place of (R)-2,8-diazabicyclo-[4.3.0]non-5-ene.2HCl to obtain 107 mg of the title compound as a yellow solid.

Element Analysis($C_{25}H_{28}N_5O_3F$) Exp. (%): C, 64.41; H, 6.31; N, 15.32 Calc. (%): C, 64.52; H, 6.02; N, 15.05

EXAMPLE 20
8-[(3-N-benzylamino-4-aminomethylpyrrolidine)-1-yl]-1-cyclopropyl-7-fluoro-9-methyl-4-oxo-4H-quinolizine-3-carboxylic acid The procedure of Example 1 was repeated except that 118 mg of 3-N-benzylamino-4-aminomethylpyrrolidine.2HCl was used as a starting material in place of (R)-2,8-diazabicyclo-[4.3.0]non-5-ene.2HCl to obtain 137 mg of the title compound as a yellow solid.

Element Analysis($C_{26}H_{29}N_4O_3F$) Exp. (%): C, 67.48; H, 6.56; N, 12.32 Calc. (%): C, 67.24; H, 6.25; N, 12.07

EXAMPLE 21
8-{[(R)-2,8-diazabicyclo[4.3.0]non-5-en]-8-yl}-1-cyclopropyl-7-fluoro-9-methoxy-4-oxo-4H-quinolizine-3-carboxylic acid The procedure of Example 1 was repeated except that 8-chloro-1-cyclopropyl-7-fluoro-9-methoxy-4-oxo-4H-quinolizine-3-carboxylic acid was used as a starting material in place of 8-chloro-1-cyclopropyl-7-fluoro-9-methyl-4-oxo-4H-quinolizine-3-carboxylic acid and the amount of (R)-2,8-diazabicyclo[4.3.0]non-5-ene.2HCl used was 80 mg to obtain 92 mg of the title compound as a yellow solid.

Element Analysis($C_{21}H_{22}N_3O_3F$) Exp. (%): C, 65.71; H, 5.73; N, 10.88 Calc. (%): C, 65.80; H, 5.74; N, 10.97

EXAMPLE 22
8-{[(S)-2,8-diazabicyclo[4.3.0]non-5-en]-8-yl}-1-cyclopropyl-7-fluoro-9-methyl-4-oxo-4H-quinolizine-3-carboxylic acid The procedure of Example 1 was repeated except that 8-chloro-1-cyclopropyl-7-fluoro-9-methoxy-4-oxo-4H-quinolizine-3-carboxylic acid and 80 mg of (S)-2,8-diazabicyclo[4.3.0]non-5-en.2HCl were used as starting materials in place of 8-chloro-1-cyclopropyl-7-fluoro-9-methyl-4-oxo-4H-quinolizine-3-carboxylic acid and 70 mg of (R)-2,8-diazabicyclo-[4.3.0]non-5-ene.2HCl, respectively, to obtain 89 mg of the title compound as a yellow solid.

Element Analysis($C_{21}H_{21}N_3O_3F_2$) Exp. (%): C, 65.86; H, 5.46; N, 10.90 Calc. (%): C, 65.97; H, 5.50; N, 10.99

EXAMPLE 23
8-[(3-N-methoxyimino-4-aminomethylpyrrolidine)-1-yl]-1-cyclopropyl-7-fluoro-9-methyl-4-oxo-4H-quinolizine-3-carboxylic acid The procedure of Example 1 was repeated except that 104 mg of 3-N-methoxyimino-4-aminomethylpyrrolidine was used as a starting material in place of 70 mg of (R)-2,8-diazabicyclo-[4.3.0]non-5-ene.2HCl to obtain 142 mg of the title-compound as a yellow solid.

Element Analysis($C_{20}H_{23}N_4O_4F$) Exp. (%): C, 59.92; H, 5.73; N, 13.97 Calc. (%): C, 59.70; H, 5.72; N, 13.93

Test 1. Antibacterial activity in vitro

In order to measure antibacterial activities of the compounds of the present invention, minimal inhibitory concentrations(MIC, µg/ml) of representative compounds against standard strains were determined and compared with ciprofloxacin and sparfloxacin, which were used as control compounds.

The MIC values were determined employing a two-fold dilution method and Muller Hinton agar medium. Each of the Hoechst 345 standard strains having the concentration of $10^7$ CFU/ml was inoculated onto the medium, and incubated at 37° C. for 18 hours.

The standard test strains used are as follows:

Gram-Positive Bacteria

1. *Streptococcus pyogenes* A 308
2. *Streptococcus pyogenes* A 77
3. *Streptococcus faecium* MD 8b
4. *Staphylococcus aureus* SG 511
5. *Staphylococcus aureus* 285
6. *Staphylococcus aureus* 503

Gram-Negative Bacteria

7. *Escherichia coli* 078
8. *Escherichia coli* DC 0
9. *Escherichia coli* DC 2
10. *Escherichia coli* TEM
11. *Escherichia coli* 1507 E
12. *Pseudomonas aeruginosa* 9027
13. *Pseudomonas aeruginosa* 1592 E
14. *Pseudomonas aeruginosa* 1771
15. *Pseudomonas aeruginosa* 1771 M
16. *Salmonella typhimurium*
17. *Klebsiella oxytoca* 1082 E
18. *Klebsiella aerogenes* 1552 E
19. *Enterobacter cloacae* P 99
20. *Enterobacter cloacae* 1321 E The results of the MIC tests are shown in Table I.

TABLE I

| Minimal Inhibitory Concentration (MIC) µg/ml | | | | |
|---|---|---|---|---|
| | Compound of Example | | Cipro- | Spar- |
| | 1 | 16 | floxacin | floxacin |
| *Streptococcus pyogenes* A 308 | 0.049 | 0.098 | 3.125 | 0.391 |
| *Streptococcus pyogenes* A 77 | 0.025 | 0.049 | 0.781 | 0.195 |
| *Streptococcus faecium* MD 8b | 0.025 | 0.049 | 0.391 | 0.391 |
| *Staphylococcus aureus* SG 511 | 0.007 | 0.013 | 0.195 | 0.098 |
| *Staphylococcus aureus* 285 | 0.013 | 0.013 | 0.781 | 0.049 |
| *Staphylococcus aureus* 503 | 0.007 | 0.013 | 0.391 | 0.049 |
| *Escherichia coli* 078 | <0.002 | <0.002 | 0.004 | 0.004 |
| *Escherichia coli* DC 0 | 0.049 | 0.098 | 0.195 | 0.195 |
| *Escherichia coli* DC 2 | 0.013 | 0.013 | 0.049 | 0.025 |
| *Escherichia coli* TEM | 0.007 | 0.007 | 0.007 | 0.013 |
| *Escherichia coli* 1507E | 0.007 | 0.013 | 0.007 | 0.025 |
| *Pseudomonas aeruginosa* 9027 | 0.195 | 0.195 | 0.195 | 0.781 |
| *Pseudomonas aeruginosa* 1592E | 0.098 | 0.195 | 0.195 | 0.781 |
| *Pseudomonas aeruginosa* 1771 | 0.098 | 0.195 | 0.195 | 0.781 |
| *Pseudomonas aeruginosa* 1771M | 0.049 | 0.098 | 0.049 | 0.195 |
| *Salmonella typhimurium* | 0.004 | 0.004 | 0.007 | 0.007 |
| *Klebsiella oxytoca* 1082E | <0.002 | <0.002 | <0.002 | <0.002 |
| *Klebsiella aerogenes* 1552E | 0.013 | 0.013 | 0.013 | 0.025 |
| *Enterobacter cloacae* P99 | 0.004 | 0.004 | 0.007 | 0.007 |
| *Enterobacter cloacae* 1321E | <0.002 | <0.002 | <0.002 | 0.004 | note:
ciprofloxacin: 1-cyclopropyl-6-fluoro-7-(piperazin-1-yl)-4-oxoquinoline-3-carboxylic acid
sparfloxacin: 1-cyclopropyl-5-amino-6,8-difluoro-7-(3,5-dimethylpiperazin-1-yl)-4-oxoquinoline-3-carboxylic acid Test 2. Selectivity Index Selectivity indexes of the compounds of the present invention and control compounds were measured using gyrase purified from of *E. coli* and calf thymus topoisomerase II obtained from Topogen. Co.

The selectivity index (S.I.) was calculated by the equation 1.

$$\text{S. I.} = \frac{IC_{100,\text{Topo II}}}{IC_{100,\text{Gyrase}}} \qquad \text{(Eq. 1)}$$

wherein, $IC_{100,\text{Topo II}}$ is the concentration of a compound to inhibit the enzyme activity of topoisomerase II and $IC_{100,\text{Gyrase}}$ is the concentration of a compound to inhibit the enzyme activity of gyrase of *E. coli*.

The results are shown in Table II.

TABLE II

Selectivity Index

| | $IC_{100,\text{Topo II}}$ | $IC_{100,\text{Gyrase}}$ | S.I. |
|---|---|---|---|
| Example 1 | 1,000 | 0.5 | 2,000 |
| Example 16 | 1,000 | 0.5 | 2,000 |
| Ciprofloxacin | 500 | 0.5 | 1,000 |
| Sparfloxacin | 500 | 1.0 | 500 |

As can be seen from Tables I and II, the quinolizine carboxylic acid derivatives of the present invention generally exhibit excellent antibacterial activities against Gram-positive and Gram-negative bacteria and much lower toxicity as compared with the known compounds.

While the embodiments of the subject invention have been described and illustrated, it is obvious that various changes and modifications can be made therein without departing from the spirit of the present invention which should be limited only by the scope of the appended claims.

What is claimed is:

1. A 4-oxo-quinolizine carboxylic acid derivative of formula (I) or a pharmaceutically acceptable salt thereof:

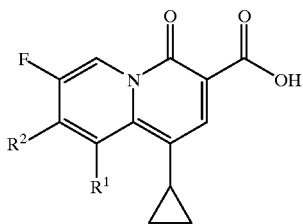

(I)

wherein $R^1$ is a $C_{1-4}$ alkyl group optionally substituted with one ore more halogens, or a $C_{1-4}$ alkoxy group;

$R^2$ is

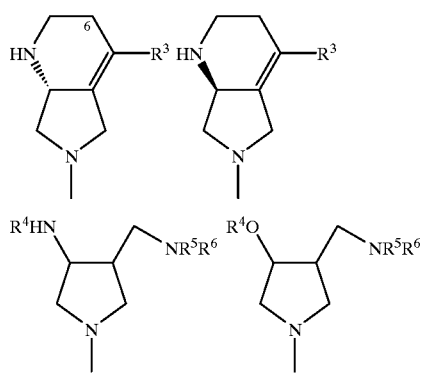

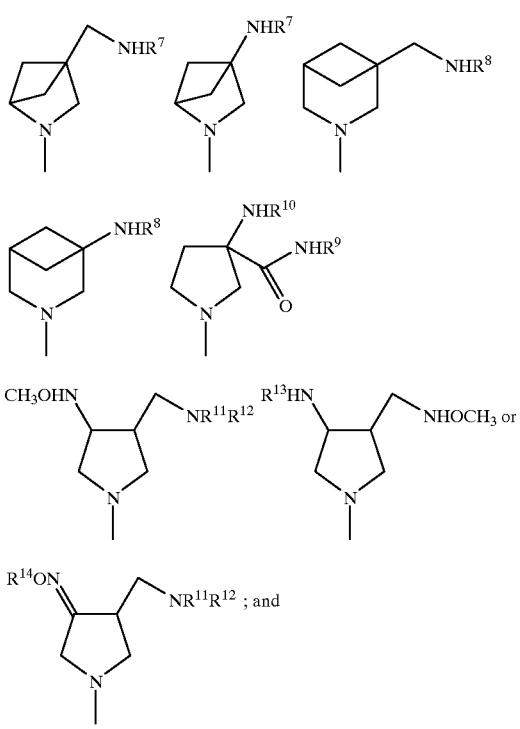

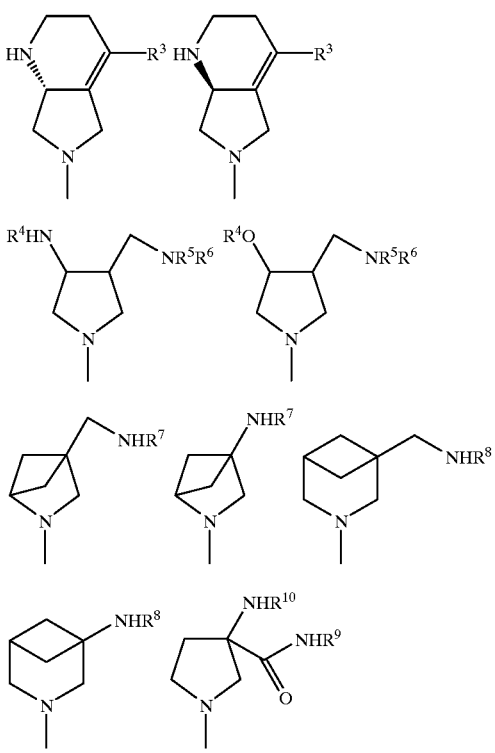

$R^3$, $R^4$, $R^5$, $R^6$, $R^7$, $R^8$, $R^9$, $R^{10}$, $R^{11}$, $R^{12}$, $R^{13}$ and $R^{14}$ are each independently H or a $C_{1-4}$ alkyl group optionally substituted with a pyridyl, arylalkyl or aryl group.

2. The quinolizine carboxylic acid derivative of claim 1, wherein: $R^1$ is $CH_3$ or $OCH_3$; $R^2$ is -continued

[Chemical structures showing pyrrolidine derivatives with substituents CH₃OHN, NR¹¹R¹², R¹³HN, NHOCH₃, R¹⁴ON, NR¹¹R¹²]

$R^3$, $R^5$, $R^6$, $R^8$, $R^{11}$ and $R^{12}$ are each independently H or CH₃; $R^4$ is H or a methyl group optionally substituted with a pyridyl or benzyl group; $R^7$, $R^9$, $R^{10}$ and $R^{13}$ are H or CH₃; and $R^{14}$ is CH₃.

3. The quinolizine carboxylic acid derivative of claim 1, selected from the group consisting of:

8-{[(R)-2,8-diazabicyclo[4.3.0]non-5-en]-8-yl)-1-cyclopropyl-7-fluoro-9-methyl-4-oxo-4H-quinolizine-3-carboxylic acid;

8-{[(S)-2,8-diazabicyclo[4.3.0]non-5-en]-8-yl}-1-cyclopropyl-7-fluoro-9-methyl-4-oxo-4H-quinolizine-3-carboxylic acid;

8-{[(R)-5-methyl-2,8-diazabicyclo[4.3.0]non-5-en]-8-yl}-1-cyclopropyl-7-fluoro-9-methyl-4-oxo-4H-quinolizine-3-carboxylic acid;

8-[(1-aminomethyl-3-azabicyclo[2.1.1]hex)-3-yl]-1-cyclopropyl-7-fluoro-9-methyl-4-oxo-4H-quinolizine-3-carboxylic acid;

8-[(1-amino-3-azabicyclo[2.1.1]hex)-3-yl]-1-cyclopropyl-7-fluoro-9-methyl-4-oxo-4H-quinolizine-3-carboxylic acid;

8-[(1-amino-3-azabicyclo[3.1.1]hept)-3-yl]-1-cyclopropyl-7-fluoro-9-methyl-4-oxo-4H-quinolizine-3-carboxylic acid;

8-[(1-aminomethyl-3-azabicyclo[3.1.1]hept)-3-yl]-1-cyclopropyl-7-fluoro-9-methyl-4-oxo-4H-quinolizine-3-carboxylic acid;

8-[(1-N-methylaminomethyl-3-azabicyclo[3.1.1]-hept)-3-yl]-1-cyclopropyl-7-fluoro-9-methyl-4-oxo-4H-quinolizine-3-carboxylic acid;

8-[(1-N-methylamino-3-azabicyclo[3.1.1]hept)-3-yl]-1-cyclopropyl-7-fluoro-9-methyl-4-oxo-4H-quinolizine-3-carboxylic acid;

8-[(3-amino-3-carbamoylpyrrolidine)-1-yl]-1-cyclopropyl-7-fluoro-9-methyl-4-oxo-4H-quinolizine-3-carboxylic acid;

8-[(3-N-methylaminomethyl-4-N-methylaminopyrrolidine)-1-yl]-1-cyclopropyl-7-fluoro-9-methyl-4-oxo-4H-quinolizine-3-carboxylic acid;

8-[(3-amino-4-aminomethylpyrrolidine)-1-yl]-1-cyclopropyl-7-fluoro-9-methyl-4-oxo-4H-quinolizine-3-carboxylic acid;

8-[(3-aminomethyl-4-N-methoxyaminopyrrolidine)-1-yl]-1-cyclopropyl-7-fluoro-9-methyl-4-oxo-4H-quinolizine-3-carboxylic acid;

8-[(3-amino-4-N-methoxyaminopyrrolidine)-1-yl]-1-cyclopropyl-7-fluoro-9-methyl-4-oxo-4H-quinolizine-3-carboxylic acid;

8-[(3-N-methoxyamino-4-N-methylaminomethylpyrrolidine]-1-yl}-1-cyclopropyl-7-fluoro-9-methyl-4-oxo-4H-quinolizine-3-carboxylic acid;

8-{[3-(3-pyridylmethyl)oxy-4-aminomethylpyrrolidine]-1-yl}-1-cyclopropyl-7-fluoro-9-methyl-4-oxo-4H-quinolizine-3-carboxylic acid;

8-{[3-(2-pyridylmethyl)oxy-4-aminomethylpyrrolidine]-1-yl}-1-cyclopropyl-7-fluoro-9-methyl-4-oxo-4H-quinolizine-3-carboxylic acid;

8-{[3-(4-pyridylmethyl)oxy-4-aminomethylpyrrolidine]-1-yl}-1-cyclopropyl-7-fluoro-9-methyl-4-oxo-4H-quinolizine-3-carboxylic acid;

8-{[3-N-(3-pyridylmethyl) amino-4-aminomethylpyrrolidine]-1-yl}-1-cyclopropyl-7-fluoro-9-methyl-4-oxo-4H-quinolizine-3-carboxylic acid;

8-[(3-N-benzylamino-4-aminomethylpyrrolidine)-1-yl]-1-cyclopropyl-7-fluoro-9-methyl-4-oxo-4H-quinolizine-3-carboxylic acid;

8-{[(R)-2,8-diazabicyclo[4.3.0]non-5-en]-8-yl}-1-cyclopropyl-7-fluoro-9-methoxy-4-oxo-4H-quinolizine-3-carboxylic acid;

8-{[(S)-2,8-diazabicyclo[4.3.0]non-5-en]-8-yl}-1-cyclopropyl-7-fluoro-9-methoxy-4-oxo-4H-quinolizine-3-carboxylic acid; and 8-[(3-N-methoxyimino-4-aminomethylpyrrolidine)-1-yl]-1-cyclopropyl-7-fluoro-9-methyl-4-oxo-4H-quinolizine-3-carboxylic acid; and pharmaceutically acceptable salts thereof.

4. A process for preparing a quinolizine carboxylic acid derivative of formula (I), which comprises reacting a compound of formula (II) with a compound of formula (III) in a solvent in the presence of a base:

[Chemical structure (I)]

[Chemical structure (II)]

$R^2H$ (III)

wherein, $R^1$ and $R^2$ have the same meanings as defined in claim 1; and X is a halogen or sulfonyl group.

5. An antibacterial composition comprising an effective amount of the quinolizine carboxylic acid derivative or a pharmaceutically acceptable salt thereof of claim 1 as an active ingredient, and a pharmaceutically acceptable carrier and/or adjuvant.

* * * * *